(12) United States Patent
Russell et al.

(10) Patent No.: US 6,905,733 B2
(45) Date of Patent: Jun. 14, 2005

(54) IRREVERSIBLE IMMOBILIZATION OF ENZYMES INTO POLYURETHANE COATINGS

(75) Inventors: Alan J. Russell, Wexford, PA (US);
Geraldine F. Drevon, Gand (BE);
Douglas Wicks, Hattiesburg, MS (US);
Karsten Danielmeier, Solingen-Burg (DE)

(73) Assignees: University of Pittsburgh, Pittsburgh, PA (US); Bayer Polymers LLC, Pittsburgh, PA (US)

( * ) Notice: Subject to any disclaimer, the term of this patent is extended or adjusted under 35 U.S.C. 154(b) by 45 days.

(21) Appl. No.: 10/202,224

(22) Filed: Jul. 24, 2002

(65) Prior Publication Data

US 2003/0129314 A1 Jul. 10, 2003

Related U.S. Application Data

(60) Provisional application No. 60/307,450, filed on Jul. 24, 2001.

(51) Int. Cl.[7] ................................................. B05D 3/00
(52) U.S. Cl. ..................................... 427/393.5; 435/177
(58) Field of Search ......................... 427/385.5; 435/177

(56) References Cited

U.S. PATENT DOCUMENTS

| 3,672,955 A | * | 6/1972 | Stanley ........................ 435/177 |
| 3,929,574 A | * | 12/1975 | Wood et al. ................... 435/43 |
| 4,195,127 A | * | 3/1980 | Hartdegen et al. ........... 435/174 |
| 4,342,834 A | | 8/1982 | Wood et al. |

FOREIGN PATENT DOCUMENTS

| GB | 1574508 | 9/1980 |
| WO | WO 03/050234 A2 | 6/2003 |

OTHER PUBLICATIONS

Drevon et al, Biomacromolecules, 1(4), pp 571–576, 2000.*
Cheng et al, CBMTS III, pp 73/1–73/8, 2000.*
Drevon et al, Biomacromolecules, 2(3), pp 644–671, 2001.*
He D, Cai Y, Wei W, Nie L, Yao S, "a–Amylase immobilized on bulk acoustic–wave sensor by UV–curing coating," Bio-Chemical Engineering Journal, vol. 6, 2000, pp. 7–11.
Kim YD, Dordick JS, Clark DS, "Siloxane–based biocatalytic films and paints for use as reactive coatings,"Biotechnology and Bioengineering, vol. 72, 2001, pp. 475–482.
Novick SJ, Dordick JS, "Protein–containing hydrophobic coatings and films," Biomaterials, vol. 23, 2002, pp. 441–448.
Arai G, Noma T, Hayashi M, Yasumori I, "Electrochemical characteristics of D–amino acid oxidase immobilized in a conductive redox polymer," Journal of Electroanalytical Chemistry, vol. 452, 1998, pp. 43–48.
Cosnier S, Fontecave M, Limosin D, Niviere V, "A poly(amphiphilic pyrrole)–flavin reductase electrode for amperometric determination of flavins," Analytical Chemistry, vol. 69, 1997, pp. 3095–3099.

(Continued)

Primary Examiner—Erma Cameron
(74) Attorney, Agent, or Firm—Thorp Reed & Armstrong LLP

(57) ABSTRACT

This invention provides a method of irreversibly immobilizing an enzyme into polyurethane coatings. This invention also provides for an enzyme-containing coating having a degree of immobilization of the enzyme of approximately 100%. The synthesis of waterborne polyurethane coatings in the presence of enzyme has enabled the irreversible attachment of the enzyme to the polymeric matrix. The distribution of immobilized enzyme as well as activity retention are homogeneous within the coating. Decreasing ECC hydrophobicity, via the use of a less hydrophobic polyisocyanate prepolymer during polymerization, significantly enhanced the intrinsic activity of the ECC.

20 Claims, 8 Drawing Sheets

OTHER PUBLICATIONS

Cosnier S, Decout J–L, Fontecave M, Frier C, Innocent C, "A reagentless biosensor for the emperometric determination of NADH," Electroanalysis, vol. 10, 1998, pp. 521–525.

Shaolin M, "Bioelectrochemical response of the polyaniline galactose oxidase electrode," Journal of Electroanalytical Chemistry, vol. 370, 1994, pp. 135–139.

Kunzelmann U, Bottcher H, "Biosensor properties of glucose oxidase immobilized within $SiO_2$ gels," Sensors and Actuators B, vol. 38–39, 1997, pp. 222–228.

Zhang Z, Liu H, Deng J, "A glucose biosensor based on immobilization of glucose oxidase in electropolymerized o–aminophenol film on platinized glassy carbon electrode," Analytical Chemistry, vol. 68, 1996, pp. 1632–1638.

Shaolin M, Huaiguo X, Bidong Q, "Bioelectrochemical responses of the polyaniline glucose oxidase electrode," Journal of Electroanalytical Chemistry, vol. 304, 1991, pp. 7–16.

Malitesta C, Palmisano F, Torsi L, Zambonin PG, "Glucose fast–response amperometric sensor based on glucose oxidase immobilized in an electropolymerized poly(o–phenylenediamine) file," Analytical Chemistry, vol. 62, 1990, pp. 2735–2740.

Yon–Hin BFY, Smolander M, Crompton T. Lowe CR, "Covalent electropolymerization of glucose oxidase in polypyrrole. Evaluation of methods of pyrrole attchement to glucose oxidase on the performance of electropolymerized glucose sensors," Analytical Biochemistry, vol. 65, 1993, pp. 2067–2071.

Foulds NC, Lowe CR, "Enzyme entrapment in electrically conducting polymers," Journal of the Chemical Society, Farady Transaction I, vol. 1, 1986, pp. 1259–1264.

Marchesiello M, Genies E, "Atheoretical model for an amperometric glucose sensor using polypyrrole as the immobilization matrix," Journal of Electroanalytical Chemistry, vol. 258, 1993, pp. 35–48.

Umana M, Waller J, "Protein–modified electrodes. The glucose oxidase/polypyrrole system," Analytical Chemistry, vol. 58, 1986, pp. 2979–2983.

Yon–Hin BFY, Lowe CR, "An Investigation of 3–funtionalized pyrrole–modified glucose oxidase for the covalent electropolymerization of enzyme files, "Journal of Electroanalytical Chemistry, vol. 374, 1994, pp. 167–172.

Wolowacz SE, Yon Hin BFY, Lowe CR, "Covalent electropolymerization of glucose oxidase in polypyrrole," Analytical Chemistry, vol. 64, 1992, pp. 1541–1545.

Cosnier S, Senillou A, Gratzel M, Comte P, Vlachopoulos N, Renault NJ, Martelet C, "A Glucose Biosensor based on enzyme entrapment within polypyrrol film electrodeposited on mesoporous titanium dioxide "Journal of Electroanalytical Chemistry, vol. 469, 1999, pp. 176–181.

Pandey PC, "A new conducting polymer–coated glucose senor," Journal of the Chemical Society, Faraday Transactions I, vol. 84, 1988, pp. 2259–2265.

Dumont J, Fortier G, "Behavior of glucose oxidase immobilized in various electropolymerized thin films," Biotechnology and Bioengineering, vol. 49, 1996, pp. 544–552.

Almeida NF, Beckman EJ, Mohammad MA, "Immobilization of glucose oxidase in thin polypyrrole films: influence of polymerization conditions and film thickness on the activity and stability of the immobilized enzyme," Biotechnology and Bioengineering, vol. 42, 1993, pp. 1037–1045.

Deng Q, Dong S, "Mediatorless hydrogen peroxide electrode based on horseradish peroxidase entrapped in poly(o–phenylenediamine)," Journal of Electroanalytical Chemistry, vol. 377, 1994, pp. 191–195.

Tatsuma T, Gondaira M, Watanabe T, "Peroxidasse–incorporated polypyrrole membrane electrodes," Analytical Chemistry, vol. 64, 1992, pp. 1183–1187.

Chen X, Wang B, Dong S, "Amperometric Biosensor for hydrogen peroxide based on sol–gel/hydrogel composite thin file," Electroanalysis, vol. 13, 2001, pp. 1149–1152.

Wang B. Zhang J, Cheng G, Dong S, "Amperometric enzyme electrode for the determination of hydrogen peroxide based on sol–gel/hydrogel composite film," Analytica Chimica Acta, vol. 407, 2000, pp. 111–118.

Wang B, Dong S, "Sol–gel derived amperometric biosensor for hydrogen peroxide based on methylene green incorporated in Nafion film," Talanta 51, 2000, pp. 565–572.

Kuncova G, Sivel M, "Lipase immobilized in organic–inorganic matrices," Journal of Sol–Gel Science and Technology, vol. 8, 1997, pp. 667–671.

Fukunaga K, Minamijima N, Sugimura Y, Zhang Z, Nakao K, "Immobilization of organic solvent–soluble lipase in nonaqueous conditions and properties of the immobilized enzymes" Journal of biotechnology, vol. 52, 1996 pp. 81–88.

Yu L, Urban G, Moser I, Jobst G, Gruber H, Photolithographically patternable modified poly(HEMA) hydrogel membrane, Polymer Bulletin, vol. 35, 1995, pp. 759–765.

Schubert F, Scheller FW, "Organelles electrodes," Methods in Enzymology, vol. 137, 1988, pp. 152–160.

Gill I, Ballesteros A, "Degradation of organophosphorous nerve agents by enzyme–polymer nanocomposites: efficient biocatalyic materials for personal protection and large–scale detoxification," Biotechnology and Bioengineering, vol. 70, 2000, pp. 400–410.

Cosnier S. Lepellec A, Guidetti B, Rico–Lattes I, "Enhancement of biosensor sensitivity in aqueous and organic solvents using a combination of poly(pyrrole–ammonium) and poly(pyrrole–lactobionamide) films as host matrices," Journal of Electoanalytical Chemistry, vol. 449, 1998, pp. 165–171.

Xue H. Shen Z, "A highly stable biosensor for phenols prepared by immobilizing polyphenol oxidase into polyaniline–polyacronitrile composite matrix," Talanta, vol. 57, 2002, pp. 289–295.

Wang B, Li B, Wang Z, Xu G, Wang Q. Dong S, "Sol–gel thin–film immobilized soybean peroxidase biosensor for the amperometric determination of hydrogen peroxide in acid medium "Analytical Chemistry vol. 71, 1999, pp. 1935–1939.

Deng Q, Guo Y, Dong S, "Cryo–hydrogel for the construction of tyrosinase–based biosensor," Analytica Chimica Acta, vol. 319, 1996, pp. 71–77.

Deng Q, Dong S, "Construction of a tyrosinase–based biosensor in pure organic phase," Analytical Chemistry, vol. 67, 1995, pp. 1357–1360.

Cosnier S, Innocent, "A new strategy for the construction of tyrosinase–based amperometric phenol and o–diphenol sensor," Bioelectrochemistry of Bioenergetics, vol. 31, 1993, pp. 147–160.

Cosnier S, Innocent C, "A novel biosensor elaboration by electropolymerization of an adsorbed amphiphillic pyrrole-tyrosinase enzyme layer," Journal of Electroanalytical Chemistry, vol. 328, 1992, pp. 361–366.

Keth E. Lejeune and Alan J. Russell, Covalent Binding of a Nerve Agent Hydrolyzing Enzyme Within Polyurethane Foams, 1996, pp. 450–457, vol. 51, XP–001155230, John Wiley & Sons, Inc.

Geraldine F. Drevon, Karsten Danielmeier, William Federspiel, Donna B. Stolz, Douglas A. Wicks, Poli C. Yu and Alan J. Russell, High–Activity Enzyme–Polyrurethane Coatings, 2002, pp. 785–794, XP–002257133, Wiley Periodicals, Inc.

* cited by examiner

IRREVERSIBLE IMMOBILIZATION OF ENZYMES INTO POLYURETHANE COATINGS

This application claims the benefit of 35 U.S.C. § 119(c) of the provisional application of U.S. Ser. No. 60/307,450 entitled "Irreversible Immobilization Of Diisopropylfluorophosphatase Into Polyurethane Coatings" filed on Jul. 24, 2001 which is incorporated herein by reference.

BACKGROUND OF THE INVENTION

1. Field of the Invention

The present invention relates to the irreversible immobilization of enzymes into polyurethane coatings.

2. State of the Art

Immobilization has been widely employed to enable and enlarge the application of enzymes as catalysts in industrial processes. Polyurethane foam has been employed as polymeric support for bioplastic synthesis with various enzymes over the last decade. Polyurethane sponge-like polymers may be synthesized from hydrophilic toluene di-isocyanate (TDI)- or methylene bis (p-phenylisocyanate) (MDI)-based polyisocyanate prepolymers and water. The incorporation of enzymes in monolithic polyurethane foam is often characterized by a degree of immobilization close to 100% and a high activity retention. Thermostability enhancement via immobilization in polyurethane foams has also been reported.

The insertion of biological molecules in coatings and thin films may drive a large range of applications. For example, potentiometric biosensors often involve the covalent attachment of enzyme onto an inner film adjacent to the sensing surface of the electrode, and the subsequent protection of the enzyme layer with an outer film. Another immobilization method for the fabrication of amperometric biosensors relies on the entrapment of enzyme in a gel layer, which is further coated by an external protective film. The lifetime and use of such systems are often limited by the diffusion of enzyme through the external membrane. To overcome this main disadvantage, the enzyme has to be directly and covalently immobilized into the coating. The covalent incorporation of biocatalyst into coatings would also be beneficial for other bioprocesses such as biocatalytic separation and filtration, microchips, and antifouling.

Direct covalent immobilization of highly-active enzymes into coatings and films has remained an elusive goal, with some of the most successful approaches exhibiting only up to 0.5% activity. Waterborne polyurethane coatings result from the polymerization of aqueous polyester based polyol dispersible aliphatic polyisocyanates. As the film is cured at room temperature, water evaporates and cross-linking occurs through the condensation between hydroxyl groups and isocyanate functionalities. Two-component waterborne polyurethanes are increasingly used in industrial applications, as they exhibit properties similar to those of solvent borne polyurethane coatings. Waterborne polyurethane coating represents a potentially ideal polymeric matrix for multipoint and covalent immobilization of enzymes.

In view of the foregoing, there is a need in the art for a method by which an enzyme can be directly added to the aqueous phase of a two-component system prior to polymerization. The immobilization process relies on the ability of amines at the enzyme surface to react with isocyanate functionalities at a faster rate than hydroxyl groups on the prepolymer.

SUMMARY OF THE INVENTION

The present invention includes a method of irreversibly immobilizing enzyme into polyurethane coatings comprising the steps of: reacting a mixture of a polyol dispersion coreactant and an enzyme to create an aqueous mixture; adding a water-dispersible aliphatic polyisocyanate based on hexamethylene diisocyanate to the aqueous mixture and reacting to produce an emulsion; applying the emulsion onto thermoplastic polyolefin panels to create an enzyme-containing coating; and curing the enzyme-containing coating.

Additionally, the present invention includes a method of irreversibly immobilizing diisopropylfluorophosphatase into polyurethane coatings comprising the steps of: reacting a mixture of a polyol dispersion coreactant having a water content of 70 w. %, a polyether modified polydimethyl siloxane surfactant, a buffered medium comprise of bis-tris propane buffer and $CaCl_2$ and diisopropylfluorophosphatase to create an aqueous mixture; adding a water-dispersible aliphatic polyisocyanate based on hexamethylene diisocyanate to the aqueous mixture and reacting to produce an emulsion; applying the emulsion onto thermoplastic polyolefin panels to create an enzyme-containing coating; and curing the enzyme-containing coating.

Also, the present invention includes an enzyme-containing coating made by the process comprising the steps of: reacting a mixture of a polyol dispersion coreactant, and an enzyme to create an aqueous mixture; adding a water-dispersible aliphatic polyisocyanate based on hexamethylene diisocyanate to the aqueous mixture and reacting to produce an emulsion; applying the emulsion onto thermoplastic polyolefin panels to create an enzyme-containing coating; and curing the enzyme-containing coating for approximately 12 hours under ambient conditions.

These and other advantages and benefits of the present invention will be apparent from the Detailed Description of the Preferred Embodiment herein below.

BRIEF DESCRIPTION OF THE DRAWINGS

For the present invention to be readily understood and practiced, the invention will now be described, for purposes of illustration and not limitation, in conjunction with the following figures wherein:

Table 1 illustrates the kinetic parameters for DFPase-containing coatings and soluble DFPase.

FIG. 2 illustrates an enzyme distribution in polyurethane coating.

DETAILED DESCRIPTION OF A PREFERRED EMBODIMENT

Figure 1:
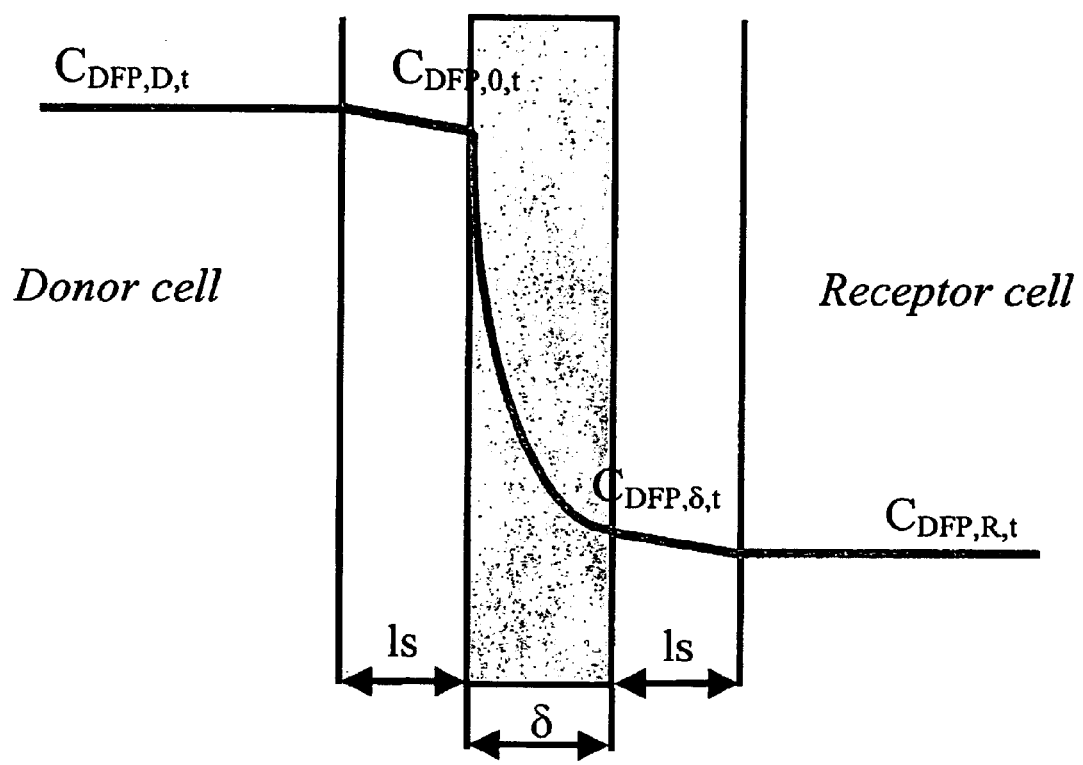
FIG. 1 illustrates a schematic of the DFP concentration profile in the case of simultaneous diffusion and enzymatic reaction in the DFPase-containing polyurethane coating.

The present invention relates to the immobilization of enzymes into waterborne polyurethane coatings. One such enzyme which may be used is diisopropylfluorophosphatase (DFPase, E.C. 3.8.2.1). However, those skilled in the art will recognize that a wide variety of enzymes and antibodies may be used. It is understood that native DFPase catalyzes the hydrolysis of toxic organophosporus nerve agents such as soman and diisopropylfluorophosphate (DFP). In the prior art, DFPase has been copolymerized into monolithic polyurethane foams with a 67% activity retention and an enhanced thermostability. Since alterations in enzyme-containing coating (ECC) hydrophilicity could influence the activity retention and stability, the immobilization process of the present invention was preformed using polyisocyanate prepolymers with various hydrophilicities. The degree to which the enzyme was irreversibly attached to the support was determined. The enzyme distribution within the coating was observed by means of gold-labeling. The influence of mass transfer on the activity of enzyme-polymers was examined using a diffusion cell apparatus. The enhancement of DFPase thermostability via immobilization was also investigated.

Material and Methods

Material

BAYHYDUR polyisocyanates XP-7063, XP-7007, XP-7148, BAYHYDROL polyol XP-7093, and Desdomodur N3400 as well as thermoplastic polyolefin (TPO) panels, used in the synthesis and curing of protein-containing coatings were kindly provided by Bayer Co. (Pittsburgh, Pa.). BAYHYDUR polyisocyanates XP-7063, XP-7007, XP-7148 are water dispersible aliphatic polyisocyanates based on hexamethylene diisocyanate (HDI). BAYHYDROL polyol XP-7093 is a polyol dispersion. The surfactant BYK-345, which is a polyether modified polydimethyl siloxane, was obtained from BYK-Chemie (Wallingford, Conn.). Di-isoproplyfluorophosphate (DFP), Bradford reagent, bovine serum albumin (BSA), Bis-Tris Propane, Tris(hydroxylmethyl)aminomethane HCl (Tris-HCl), $CaCl_2$, NaCl, $K_2CO_3$ and isopropanol were purchased from Sigma-Aldrich Chemical Co. (St. Louis, Mo.). DFPase was purchased from BioCatalytics, Inc. (Pasadena, Calif.). Polybed 812 embedding resin, which is an epoxy resin, was obtained from Polysciences (Warrington, Pa).

Method

ECC Synthesis

ECC's were prepared using buffered aqueous mixtures (10 mM Bis-Tris-Propane buffer, pH 7.5, 5 mM $CaCl_2$). Waterborne two-component polyurethanes were synthesized using water-dispersible aliphatic polyisocyanates based on hexamethylene diisocyanate (HDI) BAYHYDUR and polyol dispersion coreactants BAYHYDROL. During ECC synthesis, a ratio between isocyanate and hydroxyl functionalities of 2 was used. Typically, BAYHYDROL XP-7093 (2.5 g) (water content of 70 w. %), BYK-345 surfactant (0.1 g) and buffered medium (1.2 g) were poured into a cylindrical vessel, and followed by the addition of enzyme, DFPase(0.02–9 mg). The aqueous solution was further stirred mechanically (300 rpm) for 1 min. The amounts of BAYHYDUR XP-7063, XP-7007, XP-7148 required for ECC synthesis were calculated knowing the polyisocyanate equivalent molecular weights. When using XP-7007, the polyisocyanate (I g) was added to the aqueous solution, and the biphasic mixture was agitated for 20 s with a custom designed head attached to a 2500 rpm hand held drill. After mixing, a white emulsion with a 63 w % water content was obtained, and applied (0.45 g) on thermoplastic polyolefin (TPO) panels previously cleaned with isopropanol and dried under ambient conditions. The ECC was then allowed to cure for 12 hrs under ambient conditions and weighed again (0.24 g).

Bis-Tris-Propane contains hydroxyl groups and secondary amines, which might react with the isocyanates during the coating synthesis. The amount of buffer salt added to the reaction mixture was negligible as compared with the reactive functionalities of the polyisocyanate and polyol dispersion, and, hence, did not appear to affect the properties of the resulting two-component waterborne polyurethanes.

Protein Concentration Determination

Protein concentrations were evaluated using the Bradford reagent. The addition of the dye to protein solution at room temperature results in the formation of a dye-protein complex within fifteen (15) minutes, with an absorption maximum at 596 nm. A calibration curve with an extinction coefficient of 0.0341 ml/mg is obtained for protein concentrations ranging from 1 to 10 mg/ml.

Synthesis of Enzyme/Gold Conjugates

Gold colloids with diameters ranging from 25 to 30 nm were prepared and conjugated to DFPase in aqueous medium. Specifically, a gold solution (100 ml of 0.01% $HauCl_4.2H_2O$) was heated in a glass flask until boiling. Trisodium citrate (5 ml at 0.015%) was added and the mixture was further boiled. The colloid formation was completed when a persistent orange/red color was obtained. During conjugation the pH was adjusted slightly above the enzyme isoelectric point (pI 5.8) with $K_2CO_3$. The pH was measured with litmus paper. Typically, an enzyme weight of 0.12 g was needed to stabilize 30 ml of gold colloid solution (gold concentration: 0.01%). After addition of DFPase, the enzyme-gold solution was gently agitated, and bovine serum albumin solution (BSA) (10% (w/v)) was added to a final concentration of 0.1% (w/v). BSA blocked areas of the colloidal surface that were not coated with the enzyme. The resulting solution was centrifuged for 1 hr. at 100,000 rpm, and the enzyme-gold conjugate was recovered in the precipitate, which was resolubilized in buffered medium (10 mM Tris-HCl, pH 7.5). Centrifugation lead, to a certain extent, to the formation of gold clusters. The largest clusters that were found in dense areas of the precipitate were discarded. Smaller clusters were still present among the colloidal gold conjugates. Coatings were further prepared with BAYHYDUR XP-7007 as described above using two different concentrations of colloidal gold conjugated to enzyme (0.001 $mg_{gold}/g_{coating}$ and 0.012 $mg_{gold}/g_{coating}$).

Localization of Gold-DFPase Conjugate in Coating

To embed the films for transmission electron microscopy (TEM), small strips were washed several times in 100% ethanol then incubated in several 1 hr. changes of Polybed 812 embedding resin. It should be understood that several embedding media may be used. Most of the embedding media which may be used are based on epoxy resin and modified epoxy resin or methacrylic polymers. Films were cut into 1 mm×2 mm strips, placed in embedding molds and embedded in Polybed 812. Blocks were cured overnight at 37° C., then cured for two days at 65° C. Ultrathin cross sections (60 mm) of the films were obtained on a Reichart Ultracut E microtome. Sections were viewed on a JEOL JEM 1210 or 100CX transmission electron microscope at 80 KV.

Activity of ECC's Using a Fluoride Ion Electrode

ECC was assayed using pieces of peeled DFPase-film ranging in weight from 0.009 to 0.012 g. Typically, the pieces were placed in 10 ml of 3 mM DFP buffered solutions (5 mM $CaCl_2$ and 10 mM Bis-Tris-Propane, pH 7.5) and agitated by magnetic stirring. As DFPase acts by binding and hydrolyzing DFP (see below), the activity was measured by following fluoride release with a fluoride ion electrode at room temperature. Fluoride bulk solution concentration was measured every 20 s for 5 min.

The enzyme concentration in the coatings were varied between 0 and 2 mg/g$_{coating}$. The ECC's with higher enzyme concentrations were too active for the initial velocities to be determined.

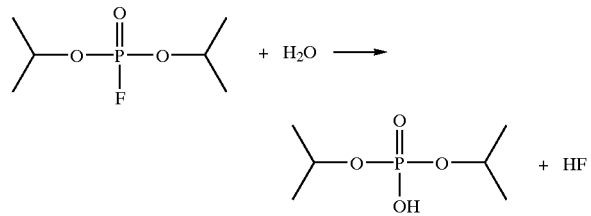

Determination of Kinetic Constants Using a Fluoride Ion Electrode

The kinetic constants were determined by means of a fluoride sensor as described in the previous section. The substrate concentrations varied from 0 to 20 mM. The data were fit to the Michaelis-Menten equation using a non-linear regression (Sigma Plot Version 2).

Diffusion Cell Experiments

The diffusion apparatus is composed of a donor and a receptor compartment, each of them being equipped with a water jacket. The diffusion system is composed of two horizontal side by side chambers with defined compartment volume (3 ml) and diffusion cross-section area (ID=9 mm). The ECC was mounted between the two compartments, and the experiments were conducted at room temperature (22° C.).

Determination of Substrate Effective Diffusion Coefficient, $D_{eff}$

The substrate effective diffusion coefficient, $D_{eff}$ (m²/min), was estimated by following the procedure, known in the art. Urease Type III (EC. 3.5.1.5), from Jack beans, which is commercially available from Sigma (St. Louis, Mo.) was immobilized into the coating (3.6 mg/g$_{coating}$) to mimic the presence of DFPase. Initially, a 3 ml volume of buffered medium (5 mM CaCl$_2$, 10 mM Bis-Tris-Propane, pH 7.5) supplemented with DFP (4 mM) was placed in the donor cell, while the receptor cell was filled with buffered medium (3 ml). Each cell was well mixed by magnetic stirring. After a fixed period of time (5–300 min), the contents were removed and diluted 4 times with buffer medium (5 mM CaCl$_2$, 10 mM Bis-Tris-Propane, pH 7.5). The DFP concentration of each sample was then determined by an activity assay with soluble DFPase. $D_{eff}$ was calculated at quasi-steady state (Equation 1).

$$[DFP]_R = \frac{D_{eff} A [DFP]_D}{V_{cell} \delta'} (t - t_0) \qquad \text{Equation 1}$$

[DFP]$_D$ and [DFP]$_R$ are the DFP concentrations in the donor and receptor cell, respectively (mol/m³). $V_{cell}$ (3·10⁻⁶ m³) and A (6.36·10⁻⁵ m²) are the cell volume and diffusion cross-section area, respectively. Assuming that the swelling of polyurethane film occurs predominantly in thickness, the thickness of wetted ECC, δ', was estimated as follows:

$$\delta' = \frac{1}{1-\epsilon} \delta \qquad \text{Equation 2}$$

The dry coating thickness, δ(10 μm), was determined using scanning electron microscopy. ϵ(0.7) is the fraction of the total volume occupied by the liquid phase in the wetted coating.

Activity Measurements

The cells were filled with buffer (5 mM CaCl$_2$, 10 mM Bis-Tris-Propane, pH 7.5). The donor cell was initially supplemented with DFP (4 mM). The initial DFP concentration in receptor cell was either 0 or 4 mM. The experiments were conducted using a fixed DFPase-ECC concentration (3.6 mg/g$_{coating}$), for which the substrate complete degradation occurred on a reasonable time scale. Each cell was well mixed by magnetic stirring. After a fixed period of time (5–120 min), the contents were removed and diluted 4 times with buffer (5 mM CaCl$_2$, 10 mM Bis-Tris-Propane, pH 7.5). The DFP concentration of each sample was then determined by an activity assay with soluble DFPase.

FIG. 1 is a schematic of the DFP concentration profile in the case of simultaneous diffusion and enzymatic reaction in the DFPase-containing coating when the receptor cell does not contain DFP at t=0 sec. ls, δ are the stagnant solution layer and the coating thickness, respectively, $C_{DFP,D,t}$, $C_{DFP,R,t}$ are the bulk DFP concentrations at a time t in the donor and receptor cell, respectively. $C_{DFP,0,t}$, $C_{DFP,\delta,t}$ are the DFP concentration in the liquid phase of coating at the surfaces and at a time t. If the diffusional resistance of boundary layer and the ECC swelling is neglected, the concentration profiles of DFP in the DFPase-ECC at unsteady state are given by Equation 3.

$$\frac{d[DFP]_{lc}}{dt} = D_{eff} \frac{d^2[DFP]_{lc}}{d^2 x} - \frac{k_{cat,int}[DFPase]_{lc}[DFP]_{lc}}{K_{M,int} + [DFP]_{lc}} \qquad \text{Equation 3}$$

[DFP]$_{lc}$, (mol/m³) is the DFP concentration in the liquid phase in the coating, $k_{cat,int}$(s⁻¹) and $K_M$(mol/m³) are the intrinsic kinetic constants for the ECC.

The initial conditions are as follows:

$x=0$ and $t=0$, $[DFP]_{lc}=0$ \qquad Equation 4

$x(x\neq 0)$ and $t=0$, $[DFP]_{lc}=0$ \qquad Equation 5

At the interface between the ECC and the donor cell we have:

$$\frac{d[DFP]_0}{dt} = \frac{AD_{eff}}{V_{cell}} \frac{d[DFP]}{dx}\bigg|_0 - (V_{Surface} + V_{Release}) \qquad \text{Equation 6}$$

Where [DFP]$_0$ represents the DFP concentration in the liquid phase at the surface of the ECC (X=0). $V_{surface}$(mol/m³.s)) represents the rate of DFP hydrolysis at the coating surface (x=0) (Equation 7), and $V_{Release}$(mol/(m³.s)) the rate of reaction catalyzed by the enzyme not covalently immobilized during the ECC synthesis and released in the donor cell (Equation 8).

$$V_{Surface} = \frac{k_{cat,int}[DFPase]_{Surface}[DFP]_0}{K_{M,int} + [DFP]_0} \qquad \text{Equation 7}$$

Where [DFPase]$_{Surface}$(mol/m³) is the number of moles of enzyme at the coating surface per unit volume of donor cell.

$$V_{Release} = \frac{k_{cat,native}[DFPase]_{Release}[DFP]_0}{K_{M,native} + [DFP]_0} \qquad \text{Equation 8}$$

Where [DFPase]$_{Release}$(mol/m³) is calculated with respect to the donor cell volume, $k_{cat,native}$ and $K_{M,native}$ are given in Table 1 (Experiment 1$^{a*}$).

Given the experimental DFP concentration profiles in donor and receptor cells Equation 2 was solved numerically using Equation 3 through 7 with Athena Visual Version 7.1.1. The intrinsic kinetic constants of the ECC, $K_{M,int}$ and $k_{catk,int}$ were then calculated.

Enzyme Modification with Desmodur N3400

DFPase-containing solution (1 ml)(50 mM MOPS, 5 mM $CaCl_2$, pH 7.5) was added to Desmodur N3400 (1 g), which is composed of the dimer and trimer of HDI. The biphasic mixture was stirred at room temperature. The activity of modified enzyme was determined by means of a fluoride sensor as described previously.

Since the degree of DFPase modification could not be determined directly, the reaction of Desmodur N3400 and enzyme Lysine residues was mimicked using Bradykinin potentiator B, a low molecular weight peptide (1182.4 Da) containing one Lysine residue. The extent of Lysine modification was determined using MALDI-TOF for various reaction time (15 min to 17 hr).

MALDI-MS analyses were performed with a Perseptive Biosystems Voyager elite MALDI-TOF. The acceleration voltage was set to 20 kV in a linear mode. The PEGylated enzyme solution (1–2 mg/ml) was mixed with an equal volume of the matrix solution (0.5 ml water, 0.5 ml acetonitrile, 2 $\mu$l TFA and 8 mg E-cyano-4-hydroxycinnamic acid), and 2 $\mu$l of the final solution was spotted on the plate target. Spectra were recorded after evaporation of the solvent mixture, and were calibrated externally with FMRP and ACTH.

DFPase modified with Desmodur N3400 was further immobilized into polyurethane coatings as described previously.

ECC Thermostability

Native and immobilized DFPase were added to buffer (10 mM BTP, 5 mM $CaCl_2$, pH 7.5) incubated at 65° C., and assayed at room temperature in buffered media (10 mM BTP, 5 mM $CaCl_2$, pH 7.5) as described above.

The thermostability of dry ECC's was determined at room temperature. After fixed periods of storage under ambient conditions, the ECC samples were assayed for activity at room temperature in buffered media (10 mM BTP, 5 mM $CaCl_2$, pH 7.5) as described above.

Results and Discussion

Reversibility of DFPase Attachment to ECC's

The extent to which DFPase is irreversibly attached to the polymer was determined using the Bradford reagent. DFPase-containing polyurethane coatings were peeled from panels, cut into small pieces, and extensively rinsed with distilled water. Less than 4% (w/w) of the protein loaded to the ECC was detected in the rinsates, indicating that the immobilization efficiency approached 100%.

Enzyme distribution in ECC's

When enzymes are incorporated into films, a key issue is whether the enzyme is equally distributed in the film. Gold labeling has been used to localize immobilized enzyme in polyurethane monolith foams in the prior art. Therefore, in the present invention DFPase was localized in ECC's via conjugation to colloidal gold particles.

FIG. 2 illustrates an enzyme distribution in polyurethane coating. Gold/DFPase-containing coatings were analyzed using dark field (A; 0.0007 $mg_{gold}/g_{coating}$) and inverse (negative) images taken using light microscopy (B; 0.0116 $mg_{gold}/g_{coating}$). Negative images were used in this case because the thickness of the coating and the high concentration of gold particles made it difficult to obtain focused images. Cross sections of the coatings were obtained using Transmission electron microscopy (C and D). The arrows with filled heads show some of the gold/enzyme particles, while the arrows with emptied heads show some of the gold/enzyme conjugate clusters. The arrowheads indicate the extremities of coating samples within the embedded resin. The stars designate some unfocussed areas as a result of high gold particle concentration and uneven surface. Bubbles in the coating are indicated by the letter h. Size bar shown in B represent panels A and B. Size bar in C and D indicate sizes in those panels.

FIGS. 2A and 2B are micrographs of gold/DFPase conjugate-containing coatings obtained by dark field microscopy (0.001 $mg_{gold}/g_{coating}$) and inverse image light microscopy (0.012 $mg_{gold}/g_{coating}$), respectively. As the concentration of immobilized colloidal gold/enzyme conjugate is increased by 12-fold it becomes apparent that the immobilized gold/enzyme complexes are uniformly distributed within the coating. The TEM's of the cross section of gold/enzyme-containing coating (0.012 $mg_{gold}/g_{coating}$) are given in FIG. 2C (originally 2500-fold enlargement) and 2D (10,000-fold magnification). Similarly to light microscopy, TEM shows that the gold/enzyme particles and clusters are randomly distributed at the microscale level. This implies that the synthesis of gold/DFPase conjugate-containing coating leads to the homogeneous immobilization of gold/DFPase complexes in the polymeric matrix. By extrapolation one can predict that the DFPase local concentration in a film should not be location dependent.

Activity of ECC's

Figure 3:
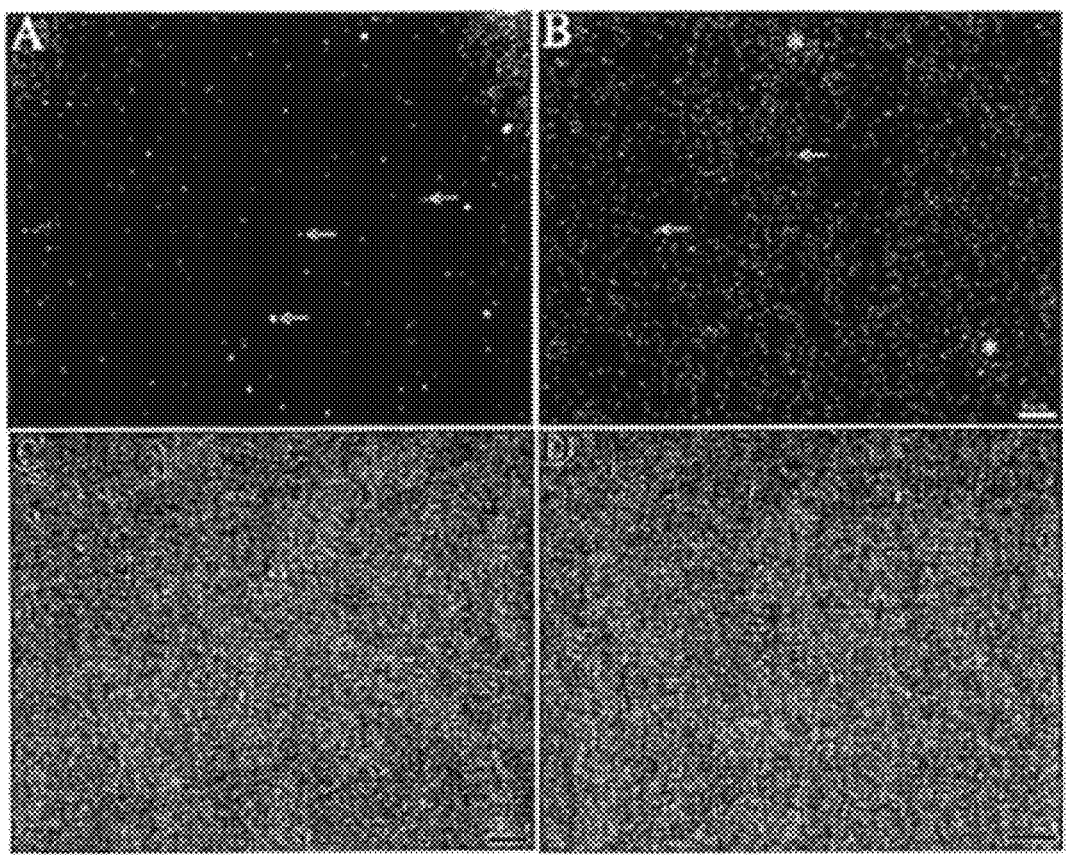
FIG. 3 illustrates the effect of DFPase concentration on DFPase-containing coating efficiency.
Figure 3:
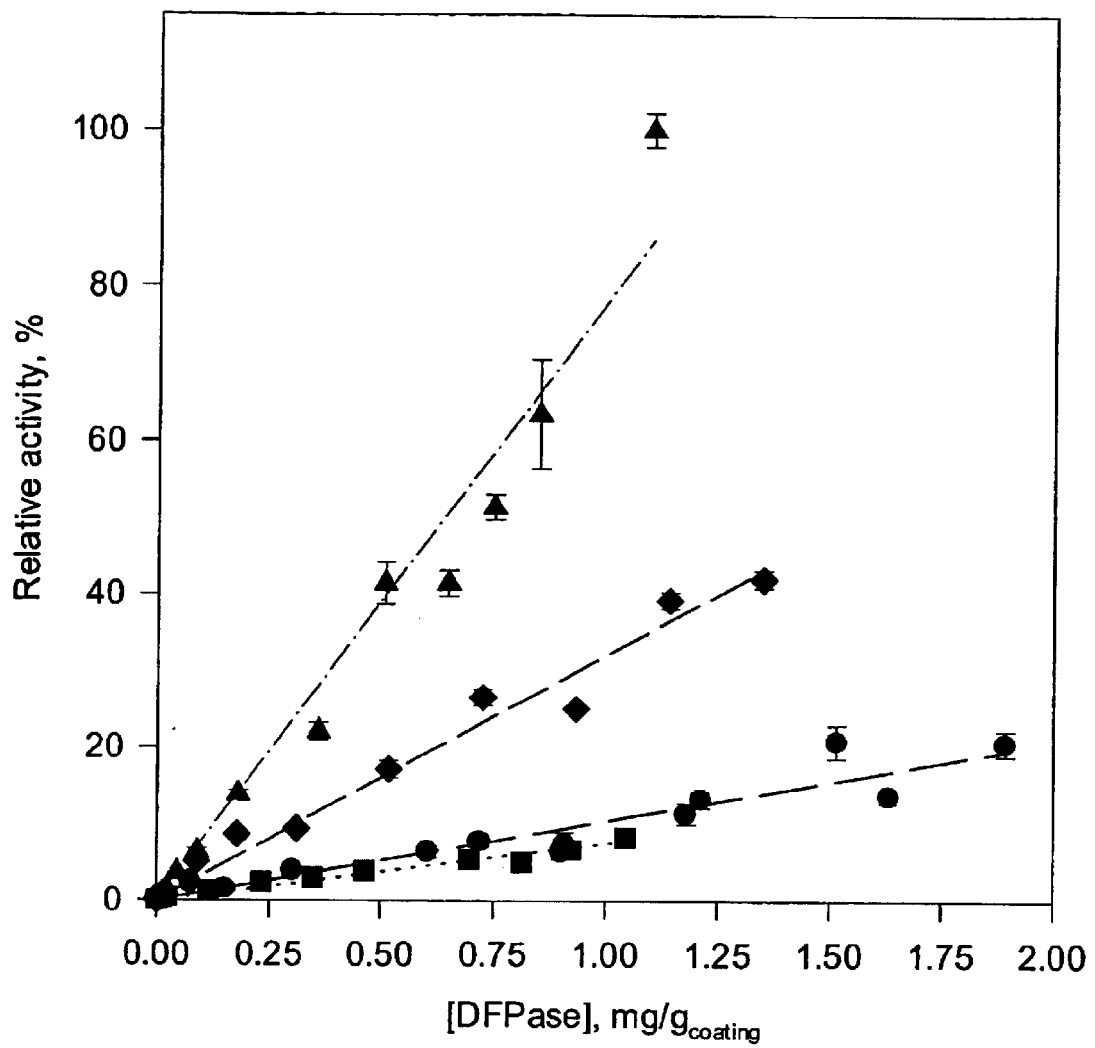
Figure 4:
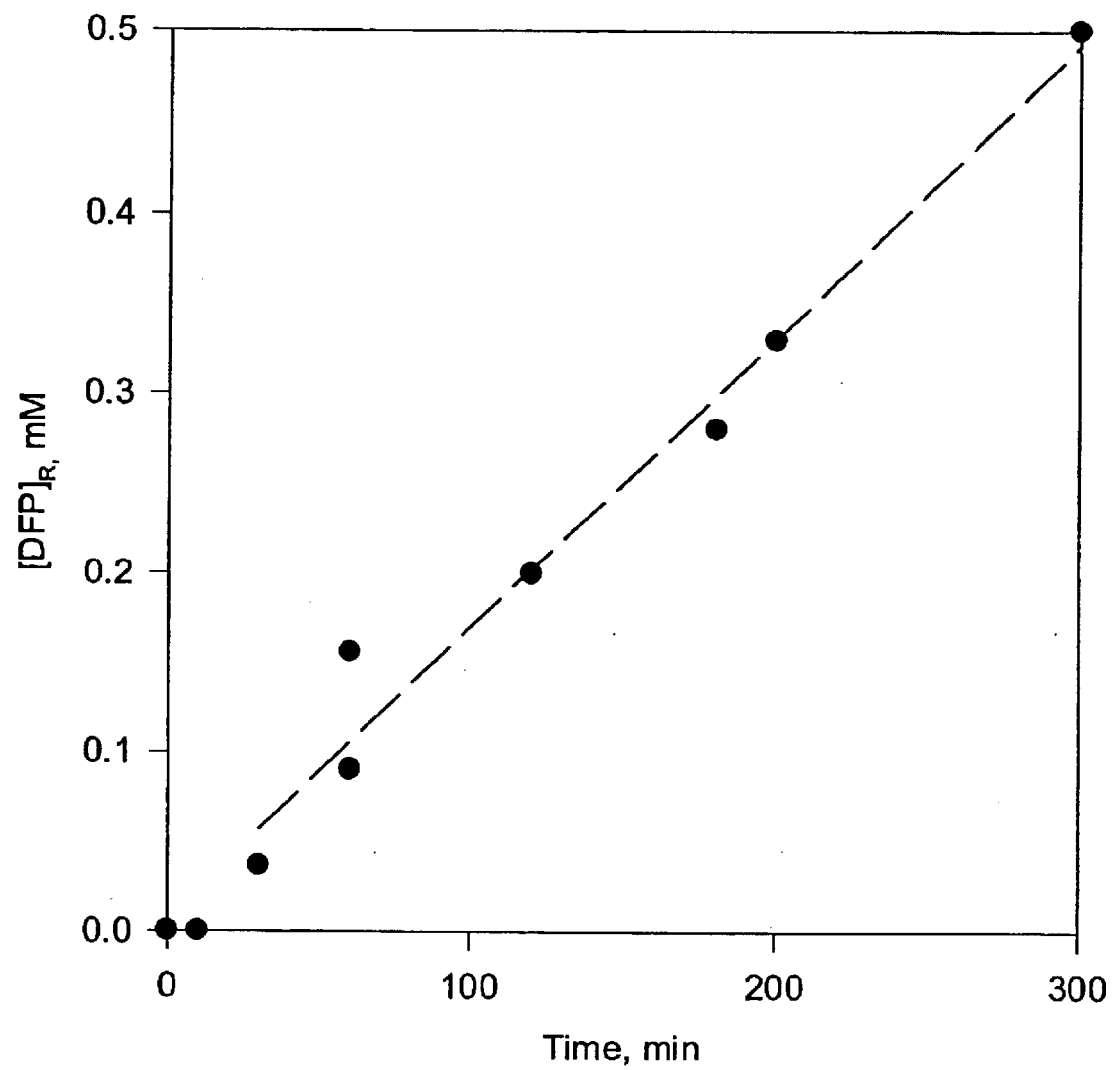
FIG. 4 illustrates the effective diffusion of DFP through coatings.

ECC's were prepared using the polyisocyanate prepolymers XP-7007, XP-7148 and XP-7063. FIG. 3 shows the activity of each ECC as a function of initial DFPase loading. The activity is directly proportional to the enzyme concentration, which implies that there is no significant mass transfer limitation. Since FIG. 2 indicates that the films are non-porous, this result implies (as we will discuss in detail later) that only enzyme in a thin external layer of the film is accessible to substrate.

The hydrophilicity of polyisocyanate decreases in the order XP-7148>XP-7063>XP-7007. Interestingly, the apparent activity retention of ECC's increases as the hydrophilicity of polyisocyanate decreases (See FIG. 3). Studies of enzyme activity in dehydrated organic solvents demonstrate that enzymes prefer hydrophobic environments. It may not be coincidental that less hydrophilic polyisocyanates are superior ECC materials. With respect to FIG. 3, coatings were synthesized with polyol XP-7093 and polyisocyanate XP-7007 (Closed diamond), XP-7063 (closed circles) and XP-7148 (closed squares) in buffered solution (10 mM bis-tris-propane, 5 mM $CaCl_2$) at pH 7.5. The closed triangles correspond to the apparent activity of coatings synthesized starting from DFPase modified with Desmodur N3400, polyol XP-7093 and polyisocyanate XP-7007. The activity of the bioplastic is reported at a 3 mM DFP concentration.

The use of polyisocyanate XP-7007 generates ECC's with the highest levels of apparent activity retention, and thus subsequent environments were preformed with XP 7007-containing-ECC's. The apparent kinetic characteristics calculated by assuming all the loaded enzyme is available (Table 1, Experiment $1^{b*}$) lead to an observable activity retention (11%) rather than intrinsic retention.

Effective Diffusivity of DFP in ECC, $D_{eff}$

To understand activity retention in ECC's the diffusivity of the substrate in the film was assessed. Using Equation 1, $D_{eff}$ was found to be $(5+/-1)\times10^{-10}$ $m^2$/min. With reference to FIG. 4, coatings were synthesized using the polyol XP-7093 and polyisocyanate XP-7007, and the experiment was conducted in buffered medium (10 mM bis-tris-propane, 5 mM $CaCl_2$) at pH 7.5 by means of a cell diffusion apparatus. It is known that $D_{\text{eff}}$ is two to three orders of magnitude lower than the diffusion coefficients of gases into liquids or organic solutes into hydrogels. Similarly, in the prior art high resistance of two-component waterborne polyurethane coatings to diffusion of chloride ions was observed. The accessibility of enzyme located within the coating to substrate is clearly limited by the low coating permeability. Once again, this result indicates that the degree of penetration of DFP into coating should be taken into account in order to determine the activity retention of ECC's.

Figure 5:
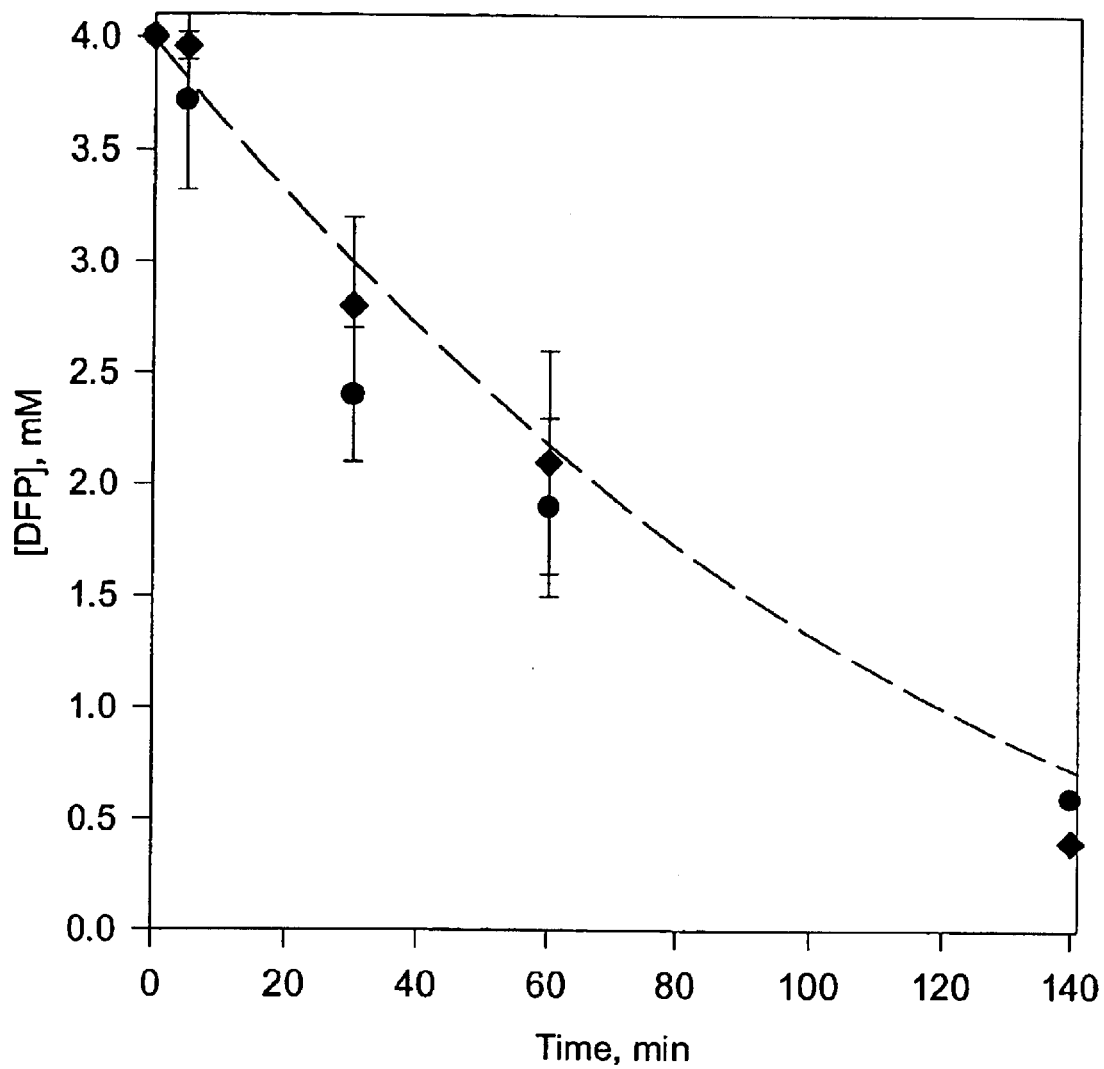
FIG. 5 illustrates profiles for DFP consumption in diffusion cells. Coatings were synthesized using the polyol XP-7093 and polyisocyanate XP-7007, and a DFPase loading of 3.6 $mg/g_{coating}$.

FIG. 5 shows the profile for DFP concentration in donor and receptor cell over time when using a DFPase-ECC (3.6 mg/g$_{coating}$), and an initial concentration of 4 mM DFP in both cells. The experiments were conducted in buffered medium (10 mM bis-tris-propane, 5 mM CaCl$_2$) at pH 7.5 using an initial DFP concentration of 4 mM in both donor and receptor cells. The DFP concentrations in donor (closed diamonds) and receptor (closed circles) cells were determined over time. The theoretical DFP profiles in the donor and receptor cells are identical due to symmetry. The experimental concentration curves in donor and receptor cells are, thus, described by the same simulated profile (dashed line) using Equations 2–7 and Athena Visual 7.1.1. The profiles for the decrease in DFP concentration in donor and receptor cells follow similar trends. Assuming immobilized DFPase is homogenously distributed in the coating (as implied in FIG. 2), the enzymatic activity retention is therefore almost the same on both sides of coating. During curing, the ECC upper and lower surfaces are in contact with the TPO panel and exposed to air, respectively. As given by the little difference in activity retention of the ECC's external surfaces, the air interface and the polymeric/hydrophobic environment do not influence the ECC activity retention.

Figure 6B:
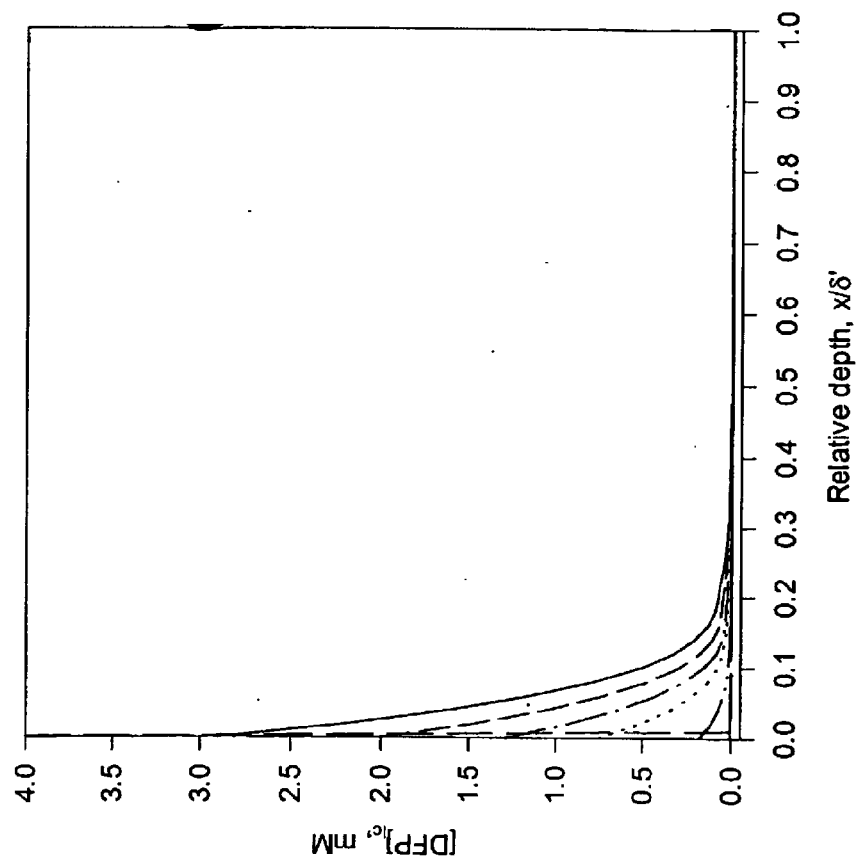
FIGS. 6a and 6b illustrates profiles for DFP consumption in diffusion cells.
Figure 6A:
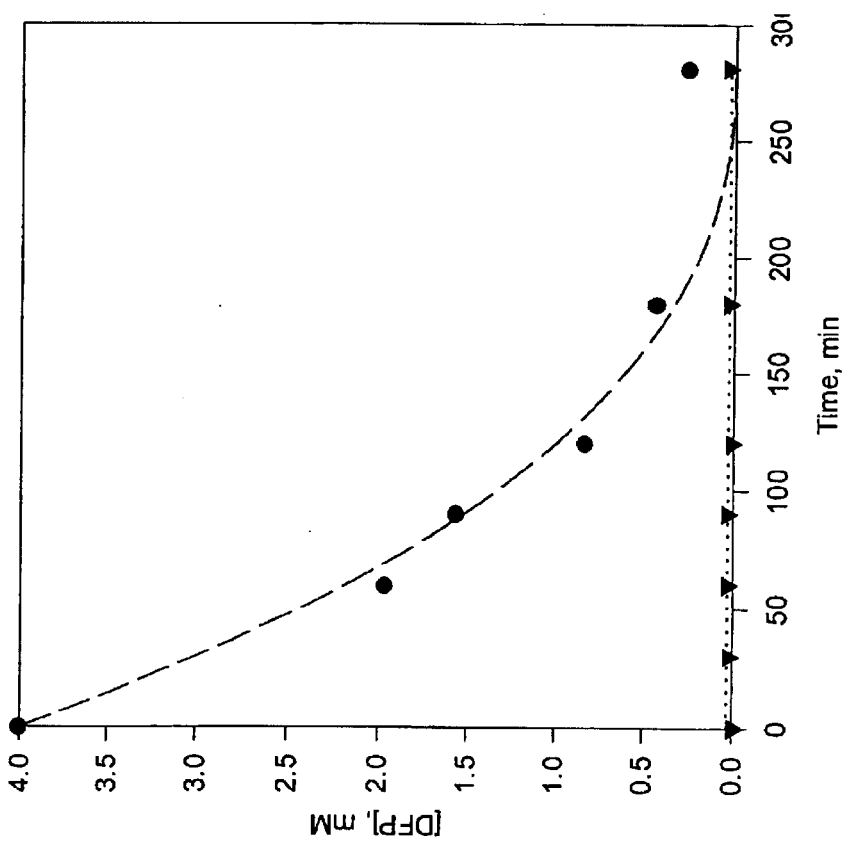

DFP concentration profiles in the donor and receptor cells were also measured for a DFPase-ECC (3.6 mg/g$_{coating}$) with no DFP in the receptor cell (See FIG. 6). Coatings were synthesized using the polyol XP-7093 and polyisocyanate XP-7007, and a DFPase loading of 3.6 mg/g$_{coating}$. The experiments were conducted in buffered medium (10 mM bis-tris-propane, 5 mM CaCl$_2$) at pH 7.5 starting with DFP (4 mM) in the donor cell and no DFP in the receptor cell. FIG. 6a shows the DFP concentrations in donor (closed diamonds) and receptor (closed circles) cells were measured over time. The simulated DFP concentration profiles in donor (dash line) and receptor (dotted line) cells were determined using Equation 2–7 and Athena Visual 7.1.1. FIG. 6b shows the substrate concentration profile in the ECC's was calculated at 0 (medium dashed line), 30 (solid line), 60 (small dashed line), 90 (dashed-dotted line), 120 (dotted line), 180 (dashed-dotted-dotted line) and 280 (long dash line). Equation 3 describes well the experimental results (FIG. 6a). The estimated intrinsic Michaelis constant of immobilized DFPase, K$_{M,int}$ (Table 1, Experiment 2$^{b**}$), is similar to that obtained without the diffusion apparatus (Table 1, Experiment 1$^{b*}$). Interestingly, by taking into account the coating resistance to substrate diffusion, k$_{cat,int}$ (Table 1, Experiment 2$^{b**}$) was found to be 2.4 times higher than the apparent k$_{cat,app}$ measured without the diffusion apparatus (Table 1, Experiment 1$^{b*}$). As shown by the simulated substrate profiles within the coating at different experimental times (FIG. 6b), the substrate penetrates a third of the coating over the time course of the experiment. Clearly, the estimation of apparent kinetic parameters involves solely the degradation of DFP in a layer of immobilized enzyme at the coating surface. Consequently, the apparent enzymatic efficiency of DFPase-ECC's is based on the activity retention of this external layer of immobilized DFPase. As given by the intrinsic kinetic constants of DFPase-ECC, the intrinsic activity retention within this layer is 38%. The ratio of apparent to intrinsic $$k_{cat}, R = \frac{k_{cat,app}}{k_{cat,int}} = 0.4,$$

gives the proportion of immobilized DFPase in ECC's reachable by the substrate during activity measurements without the diffusion apparatus.

Desmodur N3400-Modified ECC's

The vigorous mixing of Bradykinin potentiator B-containing aqueous solution with Desmodur N3400 ensured the chemical modification of the peptide Lysine residue with the dimer of HDI, as observed using MALDI-TOF. A reaction yield fluctuating between 70 and 90% was reached for a 15 min reaction time, and was not increased by further mixing of the peptide solution with the Desmodur N3400 phase.

Polyisocyanate Desmodur N3400 is based on the uretdione of HDI which is known to migrate from the bulk to the polymer/air interface during coating curing. By modifying DFPase with Desmodur N3400 prior to its immobilization into coatings, it was expected that the immobilized enzyme would be mainly concentrated within an external layer at the coating surface. Consequently, immobilized DFPase would be well accessible to substrate, leading to an increased apparent activity retention. Given the fast favorable reaction between isocyanates of the dimer of HDI and the Lysine residue of Bradykinin potentiator B, DFPase was reacted with Desmodur N3400 for 15 min. No loss of enzymatic activity was observed. As shown in FIG. 3 and Table 1 (Experiment 1b$^{#*}$), the pre-treatment of DFPase with Desmodur N3400 produced a 64% increase in apparent efficiency of ECC's.

Thermostability of ECC's

As explained in the previous section, not all of the immobilized enzyme is seen by the substrate during activity measurement. Since the inaccessible enzyme does not interfere with the rate determinations the thermal stability of the film can be determined without special consideration of diffusion resistances.

Figure 7:
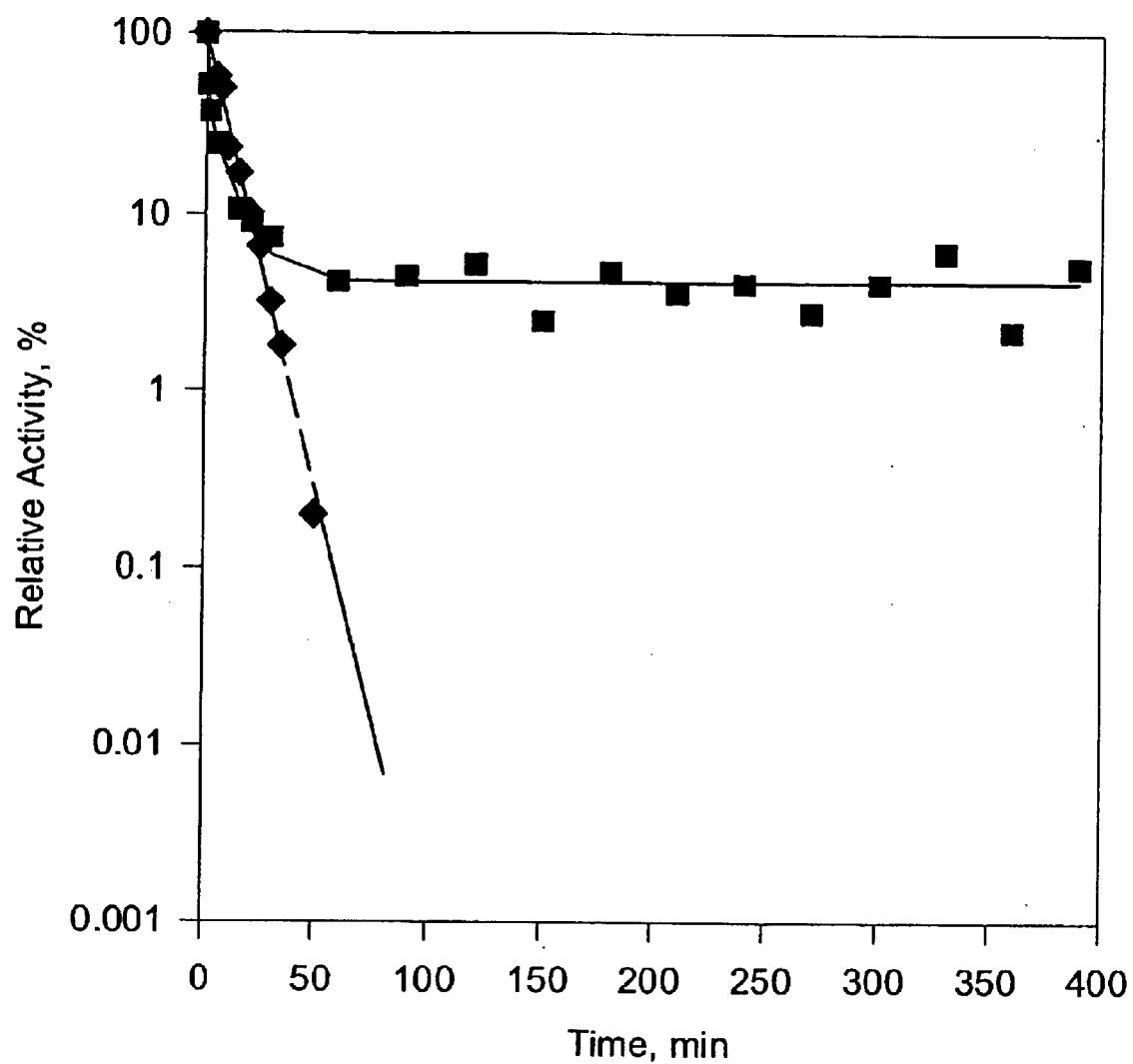
FIG. 7 illustrates the thermoinactivation of DFPase-containing coating at 65° C.

Unlike native DFPase, immobilized DFPase has a biphasic thermoinactivation profile at 65° C. (See FIG. 7). Deactivation of immobilized DFPase (closed squares) and native DFPase (closed diamonds) were conducted in buffered solution (10 mM BTP, 5 mM CaCl$_2$, pH 7.5). The remaining enzymatic activity was measured over time at room temperature in buffered media (10 mM BTP, 5 mM CaCl$_2$, pH 7.5) using DFP (3 mM) as a substrate. The biphasic behavior was described with a four parameter model, and the kinetic constants $\alpha_1$(0.34±0.03), $\alpha_2$(0.10±0.01), k$_1$(1.3±0.1) and k$_2$(0.042±0.003), were determined using the algorithm of Marquardt-Levenberg (SigmaPlot Version 2.0). An elevated temperature of 65° C. was used to inactivate the enzyme in order to perform experiments on a reasonable time scale. For this range of incubation periods, the two component polyurethane coatings did not dissolve significantly into the aqueous phase. Initially, the ECC follows a deactivation trend similar to that for native enzyme. This initial rapid deactivation leads, however, to the formation of a stable and active form of immobilized enzyme with a 6–7% residual activity. No significant change in the activity of the highly stable form of the DFPase-ECC is observed over 350 min. The biphasic deactivation kinetics of the ECC can be modeled by a four-parameter model, which assumes the following scheme:

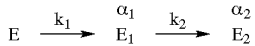

Equation 9

$E, E_1$ and $E_2$ correspond to the initial, intermediate and final state of enzyme. $\alpha_1$ and $\alpha_2$ are the residual activities of $E_1$ and $E_2$, respectively, while $k_1$ and $k_2$ represent first-order deactivation rates. The analytical solution for the enzymatic activity, a, is given by Equation 10.

$$a = \left(1 + \left(\frac{\alpha_1 k_1 - \alpha_2 k_2}{k_2 - k_1}\right)\right)\exp(-k_1 t) + \left(\frac{k_1(\alpha_2 - \alpha_1)}{k_2 - k_1}\right)\exp(-k_2 t) + \alpha_2$$

Equation 10

Where t represents the time of deactivation. The fit of the data to Equation 10 are given in FIG. 7.

Another kinetic model assuming the existence of two different forms of DFPase in ECC's with different deactivation pathways, and requiring only four physical parameters did not adequately describe the experimental data. Further more complex mechanisms were not considered as they involved five or more parameters.

The immobilization of DFPase in polyurethane foam and PEGylation also induced a transition from first order to biphasic inactivation kinetics. We believe that thermoinactivation of the DFPase-ECC results from structural changes similar to those described previously for the thermoinactivation of DFPase-containing polyurethane foam monoliths.

Figure 8:
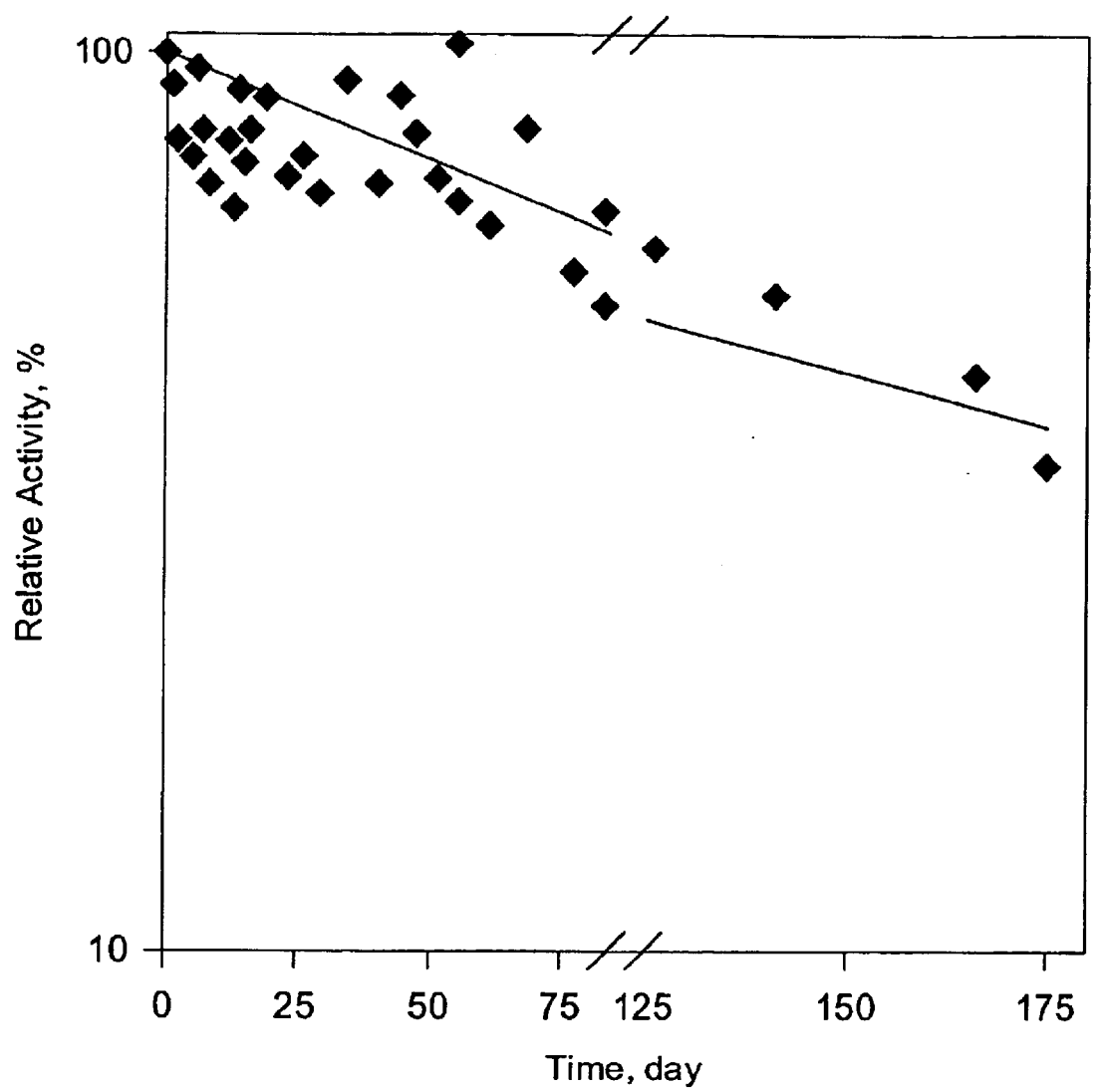
FIG. 8 illustrates the thermoactivation of DFPase-containing coating at room temperature.

DFPase-ECC's exhibit a higher stability at room temperature than at 65° C. Indeed, DFPase-ECC's lose only 40% activity after 100 days of storage at room temperature (See FIG. 8). The remaining enzymatic activity was measured over time in a buffered media (10 mM BTP, 5 mM CaCl$_2$, P.H. 7.5).using FP (mM as a substrate. Given the high stability of ECC's maintained dry under ambient conditions, the resulting catalyst should be an effective decontaminant for a variety of applications.

Therefore, covalent incorporation of DFPase into waterborne polyurethane coatings has been performed in the present invention in a single step protein-polymer synthesis using polyol and polyisocyanates. The use of polyisocyanate XP-7007 and enzyme modified with Desmodur N3400 during the immobilization process leads to the highest intrinsic catalytic efficiency (with 18 to 38% activity retention). At high temperature, DFPase-ECC's lose 93% of their activity quickly, but then become hyper-stable.

While the present invention has been described in conjunction with preferred embodiments those of ordinary skill will recognize that many modifications and variations thereof are possible. The forgoing description and the following claims are intended to cover all such modifications and

TABLE 1

Kinetic parameters for DFPase-containing coatings and soluble DFPase

| Experiment | $K_M$ (nM) | $k_{cat}$ (s$^{-1}$) | $k_{cat}/K_M$ (s$^{-1}$ · mM$^{-1}$) |
|---|---|---|---|
| 1$^{a*}$; intrinsic native DFPase | 0.79 ± 0.02 | 232 ± 2 | 293 ± 0.3 |
| 1$^{b*}$; apparent ECC | 1.3 ± 0.2 | 43 ± 3 | 33 ± 7 |

TABLE 1-continued

Kinetic parameters for DFPase-containing coatings and soluble DFPase

| Experiment | $K_M$ (nM) | $k_{cat}$ (s$^{-1}$) | $k_{cat}/K_M$ (s$^{-1}$ · mM$^{-1}$) |
|---|---|---|---|
| 1$^{b\#*}$; apparent ECC | 1.3 ± 0.2 | 70 ± 6 | 54 ± 13 |
| 2$^{b**}$; intrinsic ECC | 1.0 ± 0.1 | 211 ± 8 | 211 ± 4 |

$^a$native DFPase
$^b$polyurethane coatings
*The kinetic parameters were evaluated at room temperature in buffered media (10 mM bis-tris-propane, 5 mM CaCl$_2$, pH 7.5) using substrate concentrations varying from 0 to 20 mM and fluoride ion electrode, by applying the Michaelis-Menten equation as a model and using a non-linear regression (SigmaPlot Version 2).
$^\#$DFPase was modified with Desmodur N3400 prior to immobilization into polyurethane coatings.
**The kinetic parameters were evaluated at room temperature in buffered media (10 mM bis-tris-propane, 5 mM CaCl$_2$, pH 7.5) using the diffusion cell apparatus.

The errors on specific constants were calculated as follows:

$$\Delta\left(\frac{k_{cat}}{K_M}\right) = \left(\frac{k_{cat}}{K_M}\right) \cdot \left[\frac{\Delta k_{cat}}{k_{cat}} + \frac{\Delta K_M}{K_M}\right]$$

What is claimed is:

1. A method of irreversibly immobilizing enzymes into polyurethane coatings comprising the steps of:
   reacting a mixture of a polyol dispersion coreactant, and an enzyme to create an aqueous mixture;
   adding a water-dispersible aliphatic polyisocyanate based on hexamethylene diisocyanate to the aqueous mixture in an amount sufficient to produce an emulsion capable of forming a polyurethane coating;
   applying the emulsion onto thermoplastic polyolefin panels to create an enzyme-containing polyurethane coating; and
   curing the enzyme-containing polyurethane coating.

2. The method of claim 1 wherein the reacting a mixture step includes adding an amount of the polyol dispersion which is approximately 2 times greater than the amount of the aliphatic polyisocyanate in the adding a water-dispersible aliphatic polyisocyanante step.

3. The method of claim 2 wherein the reacting a mixture step includes adding the polyol dispersion having a water content of approximately 70 w. %.

4. The method of claim 3 wherein the reacting a mixture step includes adding a polyethylene modified polydimethyl siloxane surfactant.

5. The method of claim 4 wherein the reacting a mixture step includes adding a bis-tris propane buffer and CaCl$_2$.

6. The method of claim 5 wherein the reacting a mixture step includes adding approximately 2.5 g of the polyol dispersion coreactant and the adding a water-dispersible aliphatic polyisocyanate step includes adding approximately 1.0 g of the aliphatic polyisocyanate.

7. The method of claim 6 wherein the reacting a mixture step includes adding approximately 0.02–9 mg diisopropylfluorophosphatase.

8. The method of claim 7 including the step of reacting and modifying the diisopropylfluorophosphatase with a low viscosity aliphatic polyisocyanate resin based on hexamethylene diisocyanate prior to the reacting a mixture step.

9. A method of irreversibly immobilizing diisopropylfluorophosphatase into polyurethane coatings comprising the steps of:

reacting a mixture of a polyol dispersion coreactant having a water content of 70 w. %, a polyether modified polydimethyl siloxane surfactant, a buffered medium comprised of bis-tris-propane buffer and CaCl$_2$ and diisopropylfluorophosphatase to create an aqueous mixture;

adding a water-dispersible aliphatic polyisocyanate based on hexamethylene diisocyanate to the aqueous mixture in an amount sufficient to produce an emulsion capable of forming a polyurethane coating;

applying the emulsion onto thermoplastic polyolefin panels to create an enzyme-containing polyurethane coating; and curing the enzyme-containing polyurethane coating.

10. The method of claim 9 wherein the reacting a mixture step includes adding an amount of the polyol dispersion which is approximately 2 times greater than the amount of the aliphatic polyisocyanate in the adding a water-dispersible aliphatic polyisocyanate step.

11. The method of claim 10 including the step of reacting and modifying the diisopropylfluorophosphatase with a low viscosity aliphatic polyisocyanate resin based on hexamethylene diisocyanate prior to the reacting a mixture step.

12. An enzyme-containing composition made by the process comprising the steps of:

reacting a mixture of a polyol dispersion coreactant and an enzyme to create an aqueous mixture;

adding a water-dispersible aliphatic polyisocyanate based on hexamethylene diisocyanate to the aqueous mixture in an amount sufficient to produce an emulsion capable of forming a polyurethane coating;

applying the emulsion onto thermoplastic polyolefin panels to create an enzyme-containing polyurethane coating; and curing the enzyme-containing polyurethane coating.

13. The enzyme-containing composition of claim 12 wherein the reacting a mixture step includes adding an amount of the polyol dispersion which is approximately 2 times greater than the amount of the aliphatic polyisocyanate in the adding a water-dispersible aliphatic polyisocyanante step.

14. The enzyme-containing composition of claim 13 wherein the reacting a mixture step includes adding the polyol dispersion having a water content of approximately 70 w. %.

15. The enzyme-containing composition of claim 14 wherein the reacting a mixture step includes adding a polyethylene modified polydimethyl siloxane surfactant.

16. The enzyme-containing composition of claim 15 wherein the reacting a mixture step includes adding a bis-tris propane buffer and CaCl$_2$.

17. The enzyme-containing composition of claim 16 wherein the reacting a mixture step includes adding approximately 2.5 g of the polyol dispersion coreactant and the adding a water-dispersible aliphatic polyisocyanate step includes adding approximately 1.0 g of the aliphatic polyisocyanate.

18. The enzyme-containing composition of claim 17 wherein the reacting a mixture step includes adding approximately 0.02–9 mg diisopropylfluorophosphatase.

19. The enzyme-containing composition of claim 12 having between 10% and 100% activity retention.

20. The enzyme-containing composition of claim 12 having a degree of immobilization of the diisopropylfluorophosphatase of approximately 100%.

* * * * *

UNITED STATES PATENT AND TRADEMARK OFFICE
CERTIFICATE OF CORRECTION

PATENT NO. : 6,905,733 B2
DATED : June 14, 2005
INVENTOR(S) : Russell et al.

It is certified that error appears in the above-identified patent and that said Letters Patent is hereby corrected as shown below:

Column 4,
Line 53, delete "37°C.," and insert -- 37°C, --.

Column 5,
Line 30, delete "C.)." and insert -- C). --.
Line 32, delete "$D_{eff}$" and insert -- $D_{eff}$ --.
Line 53, delete "$[DFP\}_R$" and insert -- $[DFP]_R$ --.

Column 6,
Line 31, delete "$[DFP]_{lc}$," and insert -- $[DFP]_{lc}$ --.
Line 35, delete "$[DFP]_{lc} = 0$", third occurrence, and insert -- $[DFP]_{lc} = 4$ --.
Line 63, delete "$[DFPase\}_{Release}$" and insert -- $[DFPase]_{Release}$ --.

Column 7,
Line 2, delete "$K_{M,int}$" and insert -- $K_{M.int}$ --.
Line 23, delete "E-cyano" and insert -- α-cyano --.
Line 33, delete "65°C.," and insert -- 65°C, --.

Column 10,
Lines 44 and 55, delete "65°C." and insert -- 65°C --.

Column 11,
Line 53, after "embodiments", insert -- thereof, --.
Line 57, after "and", insert -- variations. --.

Signed and Sealed this

Second Day of May, 2006

JON W. DUDAS
*Director of the United States Patent and Trademark Office*